United States Patent
Ni et al.

(10) Patent No.: US 10,040,739 B2
(45) Date of Patent: Aug. 7, 2018

(54) METHOD FOR PREPARING DOUBLE-SEALED-END GLYCOL ETHER

(71) Applicant: Dalian Institute of Chemical Physics, Chinese Academy of Sciences, Shahekou Dalian (CN)

(72) Inventors: Youming Ni, Shahekou Dalian (CN); Wenliang Zhu, Shahekou Dalian (CN); Hongchao Liu, Shahekou Dalian (CN); Yong Liu, Shahekou Dalian (CN); Zhongmin Liu, Shahekou Dalian (CN); Lina Li, Shahekou Dalian (CN); Shiping Liu, Shahekou Dalian (CN); Hui Zhou, Shahekou Dalian (CN)

(73) Assignee: Dalian Institute of Chemical Physics, Chinese Academy of Sciences, Shahekou Dalian (CN)

( * ) Notice: Subject to any disclaimer, the term of this patent is extended or adjusted under 35 U.S.C. 154(b) by 0 days.

(21) Appl. No.: 15/537,928

(22) PCT Filed: Dec. 22, 2014

(86) PCT No.: PCT/CN2014/094535
§ 371 (c)(1),
(2) Date: Jun. 20, 2017

(87) PCT Pub. No.: WO2016/101104
PCT Pub. Date: Jun. 30, 2016

(65) Prior Publication Data
US 2017/0334818 A1 Nov. 23, 2017

(51) Int. Cl.
*C07C 41/14* (2006.01)
*B01J 29/65* (2006.01)
*B01J 29/40* (2006.01)
*B01J 29/18* (2006.01)
*B01J 29/70* (2006.01)
*B01J 29/08* (2006.01)
*C07C 43/10* (2006.01)

(52) U.S. Cl.
CPC ............ *C07C 41/14* (2013.01); *B01J 29/084* (2013.01); *B01J 29/18* (2013.01); *B01J 29/40* (2013.01); *B01J 29/65* (2013.01); *B01J 29/7007* (2013.01); *B01J 29/7038* (2013.01); *C07C 43/10* (2013.01); *Y02P 20/584* (2015.11)

(58) Field of Classification Search
CPC ...... C07C 41/14; Y02P 20/584; B01J 29/084; B01J 29/7038; B01J 29/40; B01J 29/65; B01J 29/7007; B01J 29/18
See application file for complete search history.

(56) References Cited

U.S. PATENT DOCUMENTS

| 4,321,413 A * | 3/1982 | Vanderpool ............. C07C 41/14 568/672 |
| 4,579,980 A | 4/1986 | Kogoma et al. |
| 6,316,379 B1 * | 11/2001 | Mao ........................ B01J 29/40 502/64 |
| 2004/0044253 A1 | 3/2004 | Baimbridge et al. |

FOREIGN PATENT DOCUMENTS

| CN | 101190876 A | 6/2008 |
| CN | 103641695 A | 3/2014 |
| JP | 2012149033 A | 8/2012 |

OTHER PUBLICATIONS

Matsuda et al. ("Reaction of ethylcellulose and ether or ethanol over 12-tungsophosphoric acid supported on active carbon" Sekiyu Gakkaishi, 30(3), pp. 141-148; 1987.*
Rui et al., "Synthesis of diethylene glycol dimethyl ether over williamson reaction and Optimization of Its Synthetic Conditions", Jiangxi Chemical Industry, Jan. 31, 2009, pp. 54 to 56.
Xu et al., "Synthesis of Diethylene Glycol Dimethyl Ether by Williamson Reaction", Chemical World, Jul. 31, 2006, pp. 417 to 419.
Zhang et al., "Etherification of Alcohols Over Zeolite Catalysts", Journal of Fuel Chemistry and Technology, Oct. 1997, pp. 419 to 422, vol. 25, No. 5.

\* cited by examiner

*Primary Examiner* — Rosalynd A Keys
(74) *Attorney, Agent, or Firm* — Edwin A. Sisson, Attorney at Law, LLC; Jeffrey J. Banyas

(57) ABSTRACT

Disclosed is a method for preparing a double end capped glycol ether, the method comprising: introducing into a reactor a raw material comprising a glycol monoether and a monohydric alcohol ether, and enabling the raw material to contact and react with an acidic molecular sieve catalyst to generate a double end capped glycol ether, a reaction temperature being 50-300° C., a reaction pressure being 0.1-15 MPa, a WHSV of the glycol monoether in the raw material being 0.01-15.0 $h^{-1}$, and a mole ratio of the monohydric alcohol ether to the glycol monoether in the raw material being 1-100:1. The method of the present invention enables a long single-pass lifespan of the catalyst and repeated regeneration, has a high yield and selectivity of a target product, low energy consumption during separation of the product, a high economic value of a by-product, and is flexible in production scale and application.

10 Claims, No Drawings

METHOD FOR PREPARING DOUBLE-SEALED-END GLYCOL ETHER

PRIORITIES AND CROSS REFERENCES

This Application claims priority from International Application No. PCT/CN2014/094535 filed on 22 Dec. 2014, the teachings of which are incorporated herein by reference in their entirety.

TECHNICAL FIELD

The present application belongs to the field of chemistry and chemical industry, and in particular, the present application relates to a method for preparing a double end-capped ethylene glycol ether.

TECHNICAL BACKGROUND

A double end-capped ethylene glycol ether refers to the ethylene glycol ether obtained by substituting hydrogen atoms in the two terminal hydroxyl groups of ethylene glycol with hydrocarbyl groups. The double end-capped ethylene glycol ether has no active hydrogen, and has the characteristics of strong chemical stability, low flow point, little change in viscosity-temperature, good heat resistance, strong acid-base stability, good emulsifying capability, low foam, strong lipophilic capability, good coking resistance, and lower viscosity and density. Therefore, a double end-capped polyethylene glycol ether has a wide range of applications in the fields of high-speed spinning oils, low-foaming detergents, food processing, bio-fermentation, and the like.

The preparation methods of the double end-capped ethylene glycol ether mainly comprise a synthesis method using halogenated hydrocarbons and sodium alcoholates (Williamson synthesis) and a direct etherification method. Williamson synthesis means that an ether is produced by reacting a halogenated hydrocarbon with a sodium alcoholate under anhydrous conditions, which has disadvantages of serious pollution, dangerous operation, and lower economical efficiency. The direct etherification method refers to a method of direct etherification using an ethylene glycol or an ethylene glycol monoether and a monohydric alcohol or a monohydric alcohol ether. For instance, ethylene glycol dimethyl ether may be prepared from ethylene glycol monomethyl ether and dimethyl ether by using an anion exchange resin as a catalyst (U.S. Pat. No. 4,321,413); or ethylene glycol dimethyl ether may be prepared from ethylene glycol and methanol by using a perfluorinated sulfonic acid resin as a catalyst (U.S. 2004/0044253). The catalysts used in these methods have low yield, selectivity and longevity, and it is difficult to regenerate the resin catalysts. In addition, these methods may easily produce a large amount of by-products such as 1,4-dioxane, double end-capped polyethylene glycol ethers, and the like.

SUMMARY OF THE INVENTION

According to one aspect of the present application, there is provided a method for preparing a double end-capped ethylene glycol ether. The method has the advantages in that the catalyst has a long single-pass lifespan and can be regenerated repeatedly, the yield and selectivity of the target product are high, the energy consumption for product separation is low, the by-products have high economic value, and the method is flexible in production scale and application.

The method for preparing a double end-capped ethylene glycol ether, in which a raw material containing an ethylene glycol monoether and a monohydric alcohol ether is introduced into a reactor, contacting with a catalyst containing an acidic molecular sieve and reacting to produce the double end-capped ethylene glycol ether;

wherein, the reaction temperature is in a range from 50° C. to 300° C., and the reaction pressure is in a range from 0.1 Mpa to 15 Mpa;

the weight hourly space velocity of the ethylene glycol monoether in the raw material is in a range from 0.01 h$^{-1}$ to 15.0 h$^{-1}$; and the molar ratio of the monohydric alcohol ether to the ethylene glycol monoether in the raw material is that monohydric alcohol ether:ethylene glycol monoether is in a range from 1:1 to 100:1.

As used herein, a double end-capped ethylene glycol ether refers to the ethylene glycol ether obtained by substituting hydrogen atoms in both of the two terminal hydroxyl groups of ethylene glycol with hydrocarbyl groups.

Preferably, the ethylene glycol monoether is at least one selected from the group consisting of compounds with the structure represented by Formula I:

$$R^1-O-CH_2-CH_2-OH \qquad \text{Formula I;}$$

the monohydric alcohol ether is at least one selected from the group consisting of compounds with the structure represented by Formula II:

$$R^2-O-R^2 \qquad \text{Formula II;}$$

the double end-capped ethylene glycol ether is at least one selected from the group consisting of compounds with the structure represented by Formula III:

$$R^1-O-CH_2-CH_2-O-R^2 \qquad \text{Formula III;}$$

wherein, $R^1$ is selected from the group consisting of alkyl groups with carbon atoms from 1 to 20, and $R^2$ is selected from the group consisting of alkyl groups with carbon atoms from 1 to 20.

Wherein, $R^1$ and $R^2$ may be same or different.

As used herein, an alkyl group with carbon atoms 1 to 20 refers to the group obtained by removing any one hydrogen atom from any straight chain alkane, branched alkane or cycloalkane molecule with carbon atoms 1 to 20.

The reaction equation for the preparation of the double end-capped ethylene glycol ether according to the present application is shown as follows:

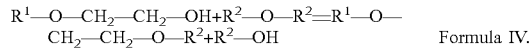
$$R^1-O-CH_2-CH_2-OH+R^2-O-R^2=R^1-O-CH_2-CH_2-O-R^2+R^2-OH \qquad \text{Formula IV.}$$

Theoretically, when the substituent $R^1$ of ethylene glycol monoether and $R^2$ of monohydric alcohol ether in the raw material are hydrocarbonyl groups having any number of carbon atoms, the preparation of the double end-capped ethylene glycol ether may be achieved in the reaction system according to the present application. Depending on the requirements for types of the product double end-capped ethylene glycol ethers, those skilled in the art can select the types of raw materials having the corresponding substituents $R^1$ and $R^2$. Preferably, $R^1$ and $R^2$ are independently selected from the group consisting of alkyl groups having not more than 10 carbon atoms. More preferably, $R^1$ and $R^2$ are independently selected from the group consisting of alkyl groups having not more than 5 carbon atoms. Still more preferably, $R^1$ and $R^2$ are independently selected from the group consisting of methyl, ethyl, n-propyl, isopropyl, and n-butyl.

Preferably, $R^1$ is any one selected from the group consisting of methyl, ethyl, n-propyl, isopropyl, and n-butyl.

Preferably, $R^2$ is any one selected from the group consisting of methyl, ethyl, n-propyl, isopropyl, and n-butyl.

Preferably, the acidic molecular sieve is one or more selected from the group consisting of molecular sieves with structural types of MWW, FER, MFI, MOR, FAU, and BEA. More preferably, the acidic molecular sieve is one or more selected from the group consisting of hydrogen-type MCM-22 molecular sieve, hydrogen-type ferrierite, hydrogen-type ZSM-5 molecular sieve, hydrogen-type mordenite, hydrogen-type Y zeolite, and hydrogen-type Beta molecular sieve.

Preferably, the atomic ratio of silicon to aluminum in the acidic molecular sieve is that Si:Al is in a range from 4:1 to 140:1.

Preferably, the upper limit of the range of reaction temperature is any one selected from the group consisting of 200° C., 250° C., and 300° C.; the lower limit of the range of reaction temperature is any one selected from the group consisting of 50° C., 90° C., and 100° C. More preferably, the reaction temperature is in a range from 100° C. to 200° C.

Preferably, the upper limit of the range of reaction pressure is any one selected from the group consisting of 8 Mpa, 10 Mpa, and 15 Mpa; and the lower limit of the range of reaction pressure is any one selected from the group consisting of 0.1 Mpa, 0.9 Mpa, 2 Mpa, 3.5 Mpa, and 4 Mpa. More preferably, the reaction pressure is in a range from 3.5 Mpa to 8 Mpa.

Preferably, the upper limit of the range of weight hourly space velocity of the ethylene glycol monoether in the raw material is any one selected from the group consisting of 5.0 $h^{-1}$, 10 $h^{-1}$, and 15 $h^{-1}$; and the lower limit of the range of weight hourly space velocity of the ethylene glycol monoether in the raw material is any one selected from the group consisting of 0.01 $h^{-1}$, 0.5 $h^{-1}$, and 1.5 $h^{-1}$. More preferably, the weight hourly space velocity of the ethylene glycol monoether in the raw material is in a range of from 0.5 $h^{-1}$ to 5.0 $h^{-1}$.

Preferably, the upper limit of the range of molar ratio of the monohydric alcohol ether to the ethylene glycol monoether in the raw material is that monohydric alcohol ether:ethylene glycol monoether is any one selected from the group consisting of 4:1, 5:1, 15:1, 25:1, 50:1, and 100:1; and the lower limit of the range of molar ratio of the monohydric alcohol ether to the ethylene glycol monoether in the raw material is that monohydric alcohol ether:ethylene glycol monoether is any one selected from the group consisting of 1:1, and 2:1. More preferably, the molar ratio of the monohydric alcohol ether to the ethylene glycol monoether in the raw material is that monohydric alcohol ether:ethylene glycol monoether is in a range from 1:1 to 5:1.

According to the present application, a carrier gas may or may not be introduced into the reaction system. The introduction of a carrier gas into the reaction system can decrease the temperature fluctuation of the catalyst bed caused by the thermal effect of the reaction system so as to maintain a more uniform temperature gradient, which facilitates to improve the reaction stability and the catalyst lifespan.

Preferably, the raw material comprises a carrier gas; and the carrier gas is one or more selected from the group consisting of nitrogen gas, helium gas and argon gas.

Preferably, gaseous hourly space velocity of the carrier gas is in a range from 0 $h^{-1}$ to 10,000 $h^{-1}$, and more preferably, gaseous hourly space velocity of the carrier gas is in a range from 100 $h^{-1}$ to 2,000 $h^{-1}$.

Preferably, the reactor contains one or more fixed bed reactors, and the reaction is performed in a form of continuous reaction. One or more fixed bed reactors may be used herein. When more than one fixed bed reactors are used, the reactors may be in series form, in parallel form, or in series and parallel form.

The beneficial effects of the present application include, but are not limited to the following effects:

a) The method provided in the present application uses an acidic molecular sieve as the catalyst, the advantages of which are that it has a long single-pass lifespan, and can be regenerated repeatedly.

b) The method provided in the present application provides markedly increased yield and selectivity for the target product as compared with the prior art.

c) The method provided in the present application does not produce water in the product, which greatly simplifies the distillation process of the product, and saves energy.

d) In the method provided by the present application, the main by-products are double end-capped diethylene glycol ether, diethylene glycol monoether and ethylene glycol having a very high economic value, with less by-products with a low economic value such as 1,4-dioxane, thereby the method is very economic.

e) The method provided by the present application has a large range of investment scale, can be applied to small and medium-sized enterprises for small-investment and small-scale production, and is flexible in application.

DETAILED DESCRIPTION OF THE EMBODIMENT

Unless otherwise specified, the raw materials and catalyst in the Examples are commercially available.

The analytical methods and the calculation method for conversion and selectivity in the Examples are as follows:

The composition of the gas/liquid phase components was analyzed automatically by using an Agilent7890 gas chromatograph configured with a gas autosampler, an FID detector and a FFAP capillary column.

In the Examples according to the present application, the conversion of ethylene glycol monoether and the selectivity for the product double end-capped ethylene glycol ether and by-products are calculated on the basis of mass:

Conversion of ethylene glycol monoether=[(mass of ethylene glycol monoether in feedstock)−(mass of ethylene glycol monoether in discharge)]/(mass of ethylene glycol monoether in feedstock)×(100%);

Selectivity for double end-capped ethylene glycol ether=(mass of double end-capped ethylene glycol ether in discharge)/[(mass of all ethylene glycol derivatives in discharge)−(mass of unreacted ethylene glycol monoether in discharge)]×(100%); and Selectivity for by-products=(mass of by-products in discharge)/[(mass of all ethylene glycol derivatives in discharge)−(mass of unreacted ethylene glycol monoether in discharge)]×(100%).

As used herein, the ethylene glycol derivatives refer to compounds containing an —O—$CH_2$—$CH_2$—O— structure in molecular formula thereof, mainly including double end-capped ethylene glycol ether, 1,4-dioxane, unreacted ethylene glycol monoether, double end-capped diethylene glycol ether, diethylene glycol monoether and ethylene glycol.

Hereinafter, the present application will be further described with reference to specific Examples. It will be appreciated that these Examples are merely illustrative of the present application and are not intended to limit the scope of the present application.

EXAMPLE 1

50 g of a hydrogen-type MCM-22 molecular sieve catalyst with a silicon/alumina ratio (Si:Al) of 45:1 was calcined under an air atmosphere in a muffle furnace at 550° C. for 5 hours. A portion of the powder sample then was compressed and pulverized to 20 to 40 mesh for activity test. 10 g of the hydrogen-type MCM-22 molecular sieve catalyst sample was weighed, placed into a stainless steel reaction tube with an internal diameter of 8.5 mm, and activated at atmospheric pressure and 550° C. with nitrogen for 4 hours. Then, the temperature (abbreviated as T) was reduced to a reaction temperature of 50° C., the molar ratio ($CH_3OCH_3$:$CH_3OCH_2CH_2OH$) of the raw materials added was 1:1, and the reaction pressure (abbreviated as P) was 0.1 Mpa. The weight hourly space velocity (abbreviated as WHSV) of ethylene glycol monoether in the raw materials was 0.01 $h^{-1}$, and a carrier gas was not used. After the reaction was stable, the product was analyzed by gas chromatography to calculate the conversion of ethylene glycol monoether and selectivity for products. The reaction conditions and results are shown in Table 1.

EXAMPLE 2

The reaction of this example was performed in the same manner as described in Example 1, except that the reaction temperature T was 90° C., the reaction pressure P was 0.9 Mpa, the molar ratio ($CH_3CH_2OCH_3CH_2$:$CH_3CH_2OCH_2CH_2OH$) of the raw materials added was 2:1, the WHSV was 0.5 $h^{-1}$, the carrier gas was nitrogen, and the gaseous hourly space velocity (abbreviated as GHSV) was 100 $h^{-1}$. The reaction conditions and results are shown in Table 1.

EXAMPLE 3

The reaction of this example was performed in the same manner as described in Example 1, except that the catalyst was hydrogen-type ferrierite molecular sieve, the Si:Al ratio was 15:1, the reaction temperature T was 300° C., the reaction pressure P was 15 Mpa, the molar ratio ($CH_3OCH_3$:$CH_3OCH_2CH_2OH$) of the raw materials added was 100:1, the WHSV was 15 $h^{-1}$, the carrier gas was nitrogen, and the GHSV was 10,000 $h^{-1}$. The reaction conditions and results were shown in Table 1.

EXAMPLE 4

The reaction of this example was performed in the same manner as described in Example 1, except that the catalyst was hydrogen-type ferrierite molecular sieve, the Si:Al ratio was 15:1, the reaction temperature T was 250° C., the reaction pressure P was 10 Mpa, the molar ratio ($CH_3CH_2CH_2OCH_2CH_2CH_3$:$CH_3CH_2CH_2OCH_2CH_2OH$) of the raw materials added was 50:1, the WHSV was 10 $h^{-1}$, the carrier gas was argon, and the GHSV was 5,000 $h^{-1}$. The reaction conditions and results were shown in Table 1.

EXAMPLE 5

The reaction of this example was performed in the same manner as described in Example 1, except that the catalyst was hydrogen-type ZSM-5 molecular sieve, the Si:Al ratio was 140:1, the reaction temperature T was 100° C., the reaction pressure P was 3.5 Mpa, the molar ratio ($CH_3OCH_3$:$CH_3OCH_2CH_2OH$) of the raw materials added was 1:1, and the WHSV was 0.5 $h^{-1}$. The reaction conditions and results were shown in Table 1.

EXAMPLE 6

The reaction of this example was performed in the same manner as described in Example 1, except that the catalyst was hydrogen-type ZSM-5 molecular sieve, the Si:Al ratio was 140:1, the reaction temperature T was 150° C., the reaction pressure P was 5 Mpa, the molar ratio (($CH_3)_2$CHOCH($CH_3)_2$:($CH_3)_2$CHOCH$_2$CH$_2$OH) of the raw materials added was 3:1, the WHSV was 2.5 $h^{-1}$, the carrier gas was nitrogen, and the GHSV was 1,000 $h^{-1}$. The reaction conditions and results were shown in Table 1.

EXAMPLE 7

The reaction of this example was performed in the same manner as described in Example 1, except that the catalyst was hydrogen-type mordenite molecular sieve, the Si:Al ratio was 4:1, the reaction temperature T was 200° C., the reaction pressure P was 8 Mpa, the molar ratio ($CH_3OCH_3$:$CH_3OCH_2CH_2OH$) of the raw materials added was 5:1, the WHSV was 5 $h^{-1}$, the carrier gas was helium, and the GHSV was 2,000 $h^{-1}$. The reaction conditions and results were shown in Table 1.

EXAMPLE 8

The reaction of this example was performed in the same manner as described in Example 1, except that the catalyst was hydrogen-type mordenite molecular sieve, the Si:Al ratio was 4:1, the reaction temperature T was 180° C., the reaction pressure P was 7 Mpa, the molar ratio ($CH_3(CH_2)_3$O($CH_2)_3$CH$_3$:$CH_3(CH_2)_3$OCH$_2$CH$_2$OH) of the raw materials added was 4:1, the WHSV was 4 $h^{-1}$, the carrier gas was helium, and the GHSV was 1,500 $h^{-1}$. The reaction conditions and results were shown in Table 1.

EXAMPLE 9

The reaction of this example was performed in the same manner as described in Example 1, except that the catalyst was hydrogen-type Y molecular sieve, the Si:Al ratio was 25:1, the reaction temperature T was 130° C., the reaction pressure P was 5 Mpa, the molar ratio ($CH_3OCH_3$:$CH_3OCH_2CH_2OH$) of the raw materials added was 2:1, the WHSV was 2 $h^{-1}$, and a carrier gas was not used. The reaction conditions and results were shown in Table 1.

EXAMPLE 10

The reaction of this example was performed in the same manner as described in Example 1, except that the catalyst was hydrogen-type Y molecular sieve, the Si:Al ratio was 25:1, the reaction temperature T was 140° C., the reaction pressure P was 6 Mpa, the molar ratio ($CH_3CH_2OCH_2CH_3$:$CH_3CH_2OCH_2CH_2OH$) of the raw materials added was 2.5:1, the WHSV was 2.5 $h^{-1}$, the carrier gas was nitrogen, and the GHSV was 500 $h^{-1}$. The reaction conditions and results were shown in Table 1.

EXAMPLE 11

The reaction of this example was performed in the same manner as described in Example 1, except that the catalyst was hydrogen-type Beta molecular sieve, the Si:Al ratio was 20:1, the reaction temperature T was 230° C., the reaction pressure P was 2 Mpa, the molar ratio ($CH_3OCH_3$:$CH_3OCH_2CH_2OH$) of the raw materials added was 15:1, the WHSV was 9 $h^{-1}$, the carrier gas was nitrogen, and the GHSV was 3,000 $h^{-1}$. The reaction conditions and results were shown in Table 1.

EXAMPLE 12

The reaction of this example was performed in the same manner as described in Example 1, except that the catalyst was hydrogen-type Beta molecular sieve, the Si:Al ratio was 20:1, the reaction temperature T was 220° C., the reaction pressure P was 3 Mpa, the molar ratio ($CH_3CH_2OCH_2CH_3$:$CH_3CH_2OCH_2CH_2OH$) of the raw materials added was 25:1, the WHSV was 6 $h^{-1}$, the carrier gas was nitrogen, and the GHSV was 1,000 $h^{-1}$. The reaction conditions and results were shown in Table 1.

TABLE 1

Reaction conditions and results of the catalytic reactions in Examples 1-12

| Example | Catalyst | Composition and molar ratio of raw materials | T P WHSV GHSV | Conversion of ethylene glycol monoether (%) | Selectivity for double end-capped ethylene glycol ether (%) | Selectivity for 1,4-dioxane (%) | Selectivity for other by-products (%) | Single-pass lifespan of catalyst (day) |
|---|---|---|---|---|---|---|---|---|
| 1 | MCM-22 | $CH_3OCH_3$:$CH_3OCH_2CH_2OH$ = 1:1 | 50° C. 0.1 MPa 0.01 $h^{-1}$ 0 $h^{-1}$ | 96.7 | 92.0 | 0.3 | 8.7 | 160 |
| 2 | MCM-22 | $CH_3CH_2OCH_3CH_2$:$CH_3CH_2OCH_2CH_2OH$ = 2:1 | 90° C. 0.9 MPa 0.5 $h^{-1}$ 100 $h^{-1}$ | 94.6 | 92.0 | 0.3 | 7.7 | 150 |
| 3 | Ferrierite | $CH_3OCH_3$:$CH_3OCH_2CH_2OH$ = 100:1 | 300° C. 15 MPa 15 $h^{-1}$ 10,000 $h^{-1}$ | 97.1 | 98.0 | 0.1 | 1.9 | 170 |
| 4 | Ferrierite | $CH_3CH_2CH_2OCH_2CH_2CH_3$:$CH_3CH_2CH_2OCH_2CH_2OH$ = 50:1 | 250° C. 10 MPa 10 $h^{-1}$ 5,000 $h^{-1}$ | 98.1 | 98.8 | 0.1 | 1.1 | 200 |
| 5 | ZSM-5 | $CH_3OCH_3$:$CH_3OCH_2CH_2OH$ = 1:1 | 100° C. 3.5 MPa 0.5 $h^{-1}$ 0 $h^{-1}$ | 96.2 | 97.6 | 0.2 | 2.2 | 210 |
| 6 | ZSM-5 | $(CH_3)_2CHOCHCH_3)_2$:$(CH_3)_2CHOCH_2CH_2OH$ = 3:1 | 150° C. 5 MPa 2.5 $h^{-1}$ 1,000 $h^{-1}$ | 98.3 | 97.2 | 0.3 | 2.5 | 150 |
| 7 | Mordenite | $CH_3OCH_3$:$CH_3OCH_2CH_2OH$ = 5:1 | 200° C. 8 MPa 5 $h^{-1}$ 2,000 $h^{-1}$ | 98.8 | 99.0 | 0.1 | 0.9 | 200 |
| 8 | Mordenite | $CH_3(CH_2)_3O(CH_2)_3CH_3$:$CH_3(CH_2)_3OCH_2CH_2OH$ = 4:1 | 180° C. 7 MPa 4 $h^{-1}$ 1,500 $h^{-1}$ | 95.5 | 97.1 | 0.3 | 2.6 | 190 |
| 9 | Y molecular sieve | $CH_3OCH_3$:$CH_3OCH_2CH_2OH$ = 2:1 | 130° C. 5 MPa 2 $h^{-1}$ 0 $h^{-1}$ | 94.3 | 96.9 | 0.2 | 2.9 | 300 |
| 10 | Y molecular sieve | $CH_3CH_2OCH_2CH_3$:$CH_3CH_2OCH_2CH_2OH$ = 2.5:1 | 140° C. 6 MPa 2.5 $h^{-1}$ 500 $h^{-1}$ | 92.0 | 95.3 | 0.4 | 4.3 | 220 |
| 11 | Beta | $CH_3OCH_3$:$CH_3OCH_2CH_2OH$ = 15:1 | 230° C. 2 MPa 9 $h^{-1}$ 3,000 $h^{-1}$ | 92.7 | 96.1 | 0.4 | 3.5 | 160 |
| 12 | Beta | $CH_3CH_2OCH_2CH_3$:$CH_3CH_2OCH_2CH_2OH$ = 25:1 | 220° C. 3 MPa 6 $h^{-1}$ 1,000 $h^{-1}$ | 93.1 | 97.1 | 0.3 | 2.6 | 150 |

Note:
The other by-products were mainly double end-capped diethylene glycol ether, diethylene glycol monoether and ethylene glycol.

COMPARATIVE EXAMPLE 1

50 g of perfluorinated sulfonic acid resin (Nafion-H) bought from DuPont Company was dried under an air atmosphere in an air dry oven at 105° C. for 12 hours. After cooling, 10 g of the sample was weighed, placed into a stainless steel reaction tube with an internal diameter of 8.5 mm for activity test, and activated at atmospheric pressure and 100° C. with nitrogen for 1 hour. Then, the catalytic reaction was performed, and the reaction temperature (T) was 130° C., the molar ratio ($CH_3OCH_3:CH_3OCH_2CH_2OH$) of the raw materials added was 2:1, the reaction pressure (P) was 5 Mpa, the weight hourly space velocity (WHSV) of methylal was 2 $h^{-1}$, and a carrier gas was not used. After the reaction was stable, the product was analyzed by gas chromatography to calculate the conversion of ethylene glycol monoether and selectivity for products. The reaction conditions and results were shown in Table 2.

COMPARATIVE EXAMPLE 2

The reaction of this example was performed in the same manner as described in Comparative example 1, except that the reaction temperature T was 140° C., the reaction pressure P was 6 Mpa, the molar ratio ($CH_3CH_2OCH_2CH_3:CH_3CH_2OCH_2CH_2OH$) of the raw materials added was 2.5:1, the WHSV was 2.5 $h^{-1}$, the carrier gas was nitrogen, and the GHSV was 500 $h^{-1}$. The reaction conditions and results were shown in Table 2.

COMPARATIVE EXAMPLE 3

The reaction of this example was performed in the same manner as described in Comparative example 1, except that the catalyst was sulfonated styrene-divinylbenzene copolymer (Amberlyst-15) resin bought from Rohm and Haas Company. The reaction conditions and results were shown in Table 2.

COMPARATIVE EXAMPLE 4

The reaction of this example was performed in the same manner as described in Comparative example 2, except that the catalyst was sulfonated styrene-divinylbenzene copolymer (Amberlyst-15) resin bought from Rohm and Haas Company. The reaction conditions and results were shown in Table 2.

COMPARATIVE EXAMPLE 5

The reaction of this example was performed in the same manner as described in Comparative example 1, except that the catalyst was sulfonated styrene-divinylbenzene copolymer strongly acidic cation exchange resin (D005) bought from Dandong Pearl Specialty Resin Co., Ltd. The reaction conditions and results were shown in Table 2.

COMPARATIVE EXAMPLE 6

The reaction of this example was performed in the same manner as described in Comparative example 2, except that the catalyst was sulfonated styrene-divinylbenzene copolymer strongly acidic cation exchange resin (D005) bought from Dandong Pearl Specialty Resin Co., Ltd. The reaction conditions and results were shown in Table 2.

TABLE 2

The reaction conditions and results of the catalytic reactions in Comparative Examples 1-6

| Comparative Example | Catalyst | Composition and molar ratio of raw materials | T P WHSV GHSV | Conversion of ethylene glycol monoether (%) | Selectivity for double end-capped ethylene glycol ether (%) | Selectivity for 1,4-dioxane (%) | Selectivity for other by-products (%) | Single-pass lifespan of catalyst (day) |
|---|---|---|---|---|---|---|---|---|
| 1 | Nafion | $CH_3OCH_3:CH_3OCH_2CH_2OH = 2:1$ | 130° C. 5 MPa 2 $h^{-1}$ 0 $h^{-1}$ | 43.6 | 63.2 | 27.8 | 9.0 | 3 |
| 2 | Nafion | $CH_3CH_2OCH_2CH_3:CH_3CH_2OCH_2CH_2OH = 2.5:1$ | 140° C. 6 MPa 2.5 $h^{-1}$ 500 $h^{-1}$ | 37.1 | 77.7 | 17.5 | 4.8 | 4 |
| 3 | Amberlyst-15 | $CH_3OCH_3:CH_3OCH_2CH_2OH = 2:1$ | 130° C. 5 MPa 2 $h^{-1}$ 0 $h^{-1}$ | 38.8 | 70.5 | 20.8 | 8.7 | 3 |
| 4 | Amberlyst-15 | $CH_3CH_2OCH_2CH_3:CH_3CH_2OCH_2CH_2OH = 2.5:1$ | 140° C. 6 MPa 2.5 $h^{-1}$ 500 $h^{-1}$ | 40.0 | 72.1 | 18.5 | 9.4 | 3 |
| 5 | D005 | $CH_3OCH_3:CH_3OCH_2CH_2OH = 2:1$ | 130° C. 5 MPa 2 $h^{-1}$ 0 $h^{-1}$ | 50.1 | 77.9 | 17.6 | 4.5 | 5 |

TABLE 2-continued

The reaction conditions and results of the catalytic reactions in Comparative Examples 1-6

| Comparative Example | Catalyst | Composition and molar ratio of raw materials | T<br>P<br>WHSV<br>GHSV | Conversion of ethylene glycol monoether (%) | Selectivity for double end-capped ethylene glycol ether (%) | Selectivity for 1,4-dioxane (%) | Selectivity for other by-products (%) | Single-pass lifespan of catalyst (day) |
|---|---|---|---|---|---|---|---|---|
| 6 | D005 | $CH_3CH_2OCH_2CH_3:CH_3CH_2OCH_2CH_2OH$ = 2.5:1 | 140° C.<br>6 MPa<br>2.5 h$^{-1}$<br>500 h$^{-1}$ | 48.5 | 79.1 | 15.8 | 5.1 | 6 |

Note:
The other by-products were mainly double end-capped diethylene glycol ether, diethylene glycol monoether and ethylene glycol.

EXAMPLE 13

The catalysts inactivated in the single-pass reactions in Examples 1, 3, 5, 7, 9 and 11 were removed and regenerated, with the regeneration conditions that the catalysts were calcined at 550° C. for 4 hours under an air atmosphere. The regenerated catalysts were used again according to the reaction conditions of the example from which the catalyst was obtained. The results were shown in Table 3.

TABLE 3

Comparison of the reaction results of the catalysts in the examples before and after regeneration

| Catalysts | Reaction conditions | Conversion of ethylene glycol monoether (%) | | Selectivity for double end-capped ethylene glycol ether (%) | |
|---|---|---|---|---|---|
| | | First reaction | After regeneration | First reaction | After regeneration |
| MCM-22 | Same as those in Example 1 | 96.7 | 97.2 | 92.0 | 93.0 |
| Ferrierite | Same as those in Example 3 | 97.1 | 97.3 | 98.0 | 98.5 |
| ZSM-5 | Same as those in Example 5 | 96.2 | 97.8 | 97.6 | 98.0 |
| Mordenite | Same as those in Example 7 | 98.8 | 98.7 | 99.0 | 99.0 |
| Y molecular sieve | Same as those in Example 9 | 94.3 | 95.0 | 96.9 | 97.5 |
| Beta | Same as those in Example 11 | 92.7 | 94.1 | 96.1 | 96.5 |

The resin catalysts of the Comparative Examples cannot be regenerated.

It will be understood that the foregoing Examples are only some examples of the present application, rather than limit the present application in any form. Although the optimized examples of the present application are illustrated as above, they are not intended to limit the present application. In view of the instant disclosure, modifications or changes may be made by those skilled in the art without departing from the spirit and purview of the present application, and those modifications or changes are equivalent embodiments of the present application, falling into the scope of the appended claims.

The invention claimed is:

1. A method for preparing a double end-capped ethylene glycol ether, in which a raw material containing an ethylene glycol monoether and a monohydric alcohol ether is introduced into a reactor, contacting with a catalyst containing an acidic molecular sieve and reacting to produce the double end-capped ethylene glycol ether;
    wherein, the reaction temperature is in a range from 50° C. to 300° C., and the reaction pressure is in a range from 0.1 Mpa to 15 Mpa;
    the weight hourly space velocity of the ethylene glycol monoether in the raw material is in a range from 0.01 h$^{-1}$ to 15.0 h$^{-1}$; and
    the molar ratio of the monohydric alcohol ether to the ethylene glycol monoether in the raw material is that monohydric alcohol ether:ethylene glycol monoether is in a range from 1:1 to 100:1.

2. The method according to claim 1, wherein the ethylene glycol monoether is at least one selected from the group consisting of compounds with the structure represented by Formula I:

R$^1$—O—CH$_2$—CH$_2$—OH                Formula I;

the monohydric alcohol ether is at least one selected from the group consisting of compounds with the structure represented by Formula II:

R$^2$—O—R$^2$                Formula II;

the double end-capped ethylene glycol ether is at least one selected from the group consisting of compounds with the structure represented by Formula III:

$R^1\text{—}O\text{—}CH_2\text{—}CH_2\text{—}O\text{—}R^2$ 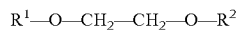 Formula III;

wherein, $R^1$ is selected from the group consisting of alkyl groups with carbon atoms from 1 to 20, and $R^2$ is selected from the group consisting of alkyl groups with carbon atoms from 1 to 20.

3. The method according to claim 2, wherein $R^1$ is any one selected from the group consisting of methyl, ethyl, n-propyl, isopropyl, and n-butyl; and $R^2$ is any one selected from the group consisting of methyl, ethyl, n-propyl, isopropyl, and n-butyl.

4. The method according to claim 1, wherein the acidic molecular sieve is one or more selected from the group consisting of molecular sieves with structural types of MWW, FER, MFI, MOR, FAU, and BEA.

5. The method according to claim 1, wherein the acidic molecular sieve includes one or more selected from the group consisting of hydrogen-type MCM-22 molecular sieve, hydrogen-type ferrierite, hydrogen-type ZSM-5 molecular sieve, hydrogen-type mordenite, hydrogen-type Y zeolite, and hydrogen-type Beta molecular sieve.

6. The method according to any one of claims 1, 4 and 5, wherein the atomic ratio of silicon to aluminum in the acidic molecular sieve is that Si:Al is in a range from 4:1 to 140:1.

7. The method according to claim 1, wherein the reaction temperature is in a range from 100° C. to 200° C., and the reaction pressure is in a range from 3.5 Mpa to 8 Mpa;

the weight hourly space velocity of the ethylene glycol monoether in the raw material is in a range from 0.5 $h^{-1}$ to 5.0 $h^{-1}$; and the molar ratio of the monohydric alcohol ether to the ethylene glycol monoether in the raw material is that monohydric alcohol ether:ethylene glycol monoether is in a range from 1:1 to 5:1.

8. The method according to claim 1, wherein the raw material contains a carrier gas;

wherein gaseous hourly space velocity of the carrier gas is in a range from 0 $h^{-1}$ to 10,000 $h^{-1}$; and the carrier gas is one or more selected from the group consisting of nitrogen gas, helium gas and argon gas.

9. The method according to claim 8, wherein the gaseous hourly space velocity of the carrier gas is in a range from 100 $h^{-1}$ to 2000 $h^{-1}$.

10. The method according to claim 1, wherein the reactor contains one or more fixed bed reactors.

* * * * *